(12) United States Patent
Dede et al.

(10) Patent No.: US 12,725,595 B2
(45) Date of Patent: Sep. 1, 2026

(54) ANISOTROPIC ELASTIC METAMATERIALS

(71) Applicant: Toyota Motor Engineering & Manufacturing North America, Inc., Plano, TX (US)

(72) Inventors: Ercan Mehmet Dede, Ann Arbor, MI (US); Yuqing Zhou, Ann Arbor, MI (US); Tsuyoshi Nomura, Novi, MI (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 1120 days.

(21) Appl. No.: 16/922,535

(22) Filed: Jul. 7, 2020

(65) Prior Publication Data

US 2022/0013098 A1 Jan. 13, 2022

(51) Int. Cl.
*G10K 11/00* (2006.01)
*B33Y 70/00* (2020.01)
(Continued)

(52) U.S. Cl.
CPC ............ *G10K 11/002* (2013.01); *G06F 30/23* (2020.01); *G10K 11/162* (2013.01); *G16C 20/30* (2019.02); *B33Y 70/00* (2014.12); *B33Y 80/00* (2014.12)

(58) Field of Classification Search
None
See application file for complete search history.

(56) References Cited

U.S. PATENT DOCUMENTS

| | | | | |
|---|---|---|---|---|
| 9,640,170 | B2 | 5/2017 | Cipolla et al. | |
| 2017/0268591 | A1* | 9/2017 | Harne | F16F 7/108 |
| 2019/0035374 | A1* | 1/2019 | Martin | G10K 11/205 |

FOREIGN PATENT DOCUMENTS

| | | | |
|---|---|---|---|
| CN | 107645664 A | * | 1/2018 |

OTHER PUBLICATIONS

Li et al., A new two-dimensional elastic metamaterial system with multiple local resonances, 2018, Elsevier, pp. 273-284 (Year: 2018).*

(Continued)

*Primary Examiner* — Ryan F Pitaro
*Assistant Examiner* — Bernard E Cothran
(74) *Attorney, Agent, or Firm* — Christopher G. Darrow; Darrow Mustafa PC

(57) ABSTRACT

Elastic metamaterial designs are provided, such as an acoustic radiator or sound partition, with non-spherical shapes or apertures defined in unit cells of an elastic medium. A method for making the same includes determining a set of boundary conditions for a plurality of non-spherical shapes/apertures defined in the elastic medium, and using a gradient-based algorithm to optimize a porous media model domain for the elastic medium, where porosity is related to size dimensions of the non-spherical shape/aperture and an anisotropic elastic modulus is related to an angle of orientation of the non-spherical shape/aperture. The method may include optimizing an objective function, and obtaining a grayscale design that relates to the porosity and the anisotropic elastic modulus. Reaction diffusion equations may be used with the grayscale design to obtain a pattern for the non-spherical shapes/apertures. Methods of manufacturing may include multi-material additive manufacturing techniques.

20 Claims, 8 Drawing Sheets

(51) Int. Cl.
*B33Y 80/00* (2015.01)
*G06F 30/23* (2020.01)
*G10K 11/162* (2006.01)
*G16C 20/30* (2019.01)

(56) References Cited

OTHER PUBLICATIONS

Yang et al., Topology optimization for the design of perfect mode-converting anisotrpic elastic metamaterials, 2018, Elsevier, pp. 161-177 (Year: 2018).*

Topology optimization for hyperbolic acoustic metamaterials using a high-frequency homogenization method, 2018, Elsevier, pp. 419-471 (Year: 2018).*

Carrara et al., Metamaterial-inspired structures and concepts for elastoacoustic wave energy harvesting, 2013, IOP Publishing, pp. 1-8 (Year: 2013).*

Merriam-Webster.com, grayscale definition, 2023, Merriam-Webster Dictionary, pp. 1-11 (Year: 2023).*

Zhang et al., Color image compression method based on reaction-diffusion equation set, Sep. 2017, European Patent Office, pp. 1-10 (Year: 2017).*

Merriam-Webster Dictionary, Homogenize, 2024, Merriam-Webster Dictionary, pp. 1-6 (Year: 2024).*

Noguchi, Y. et al., "Optimum design of an acoustic metamaterial with negative bulk modulus in an acoustic-elastic coupled system using a level set-based topology optimization method," International Journal for Numerical Methods in Engineering (Special Issue on Advanced Topology Optimization), vol. 113, Issue 8, Jul. 5, 2017, 2 pages (Summary only).

* cited by examiner

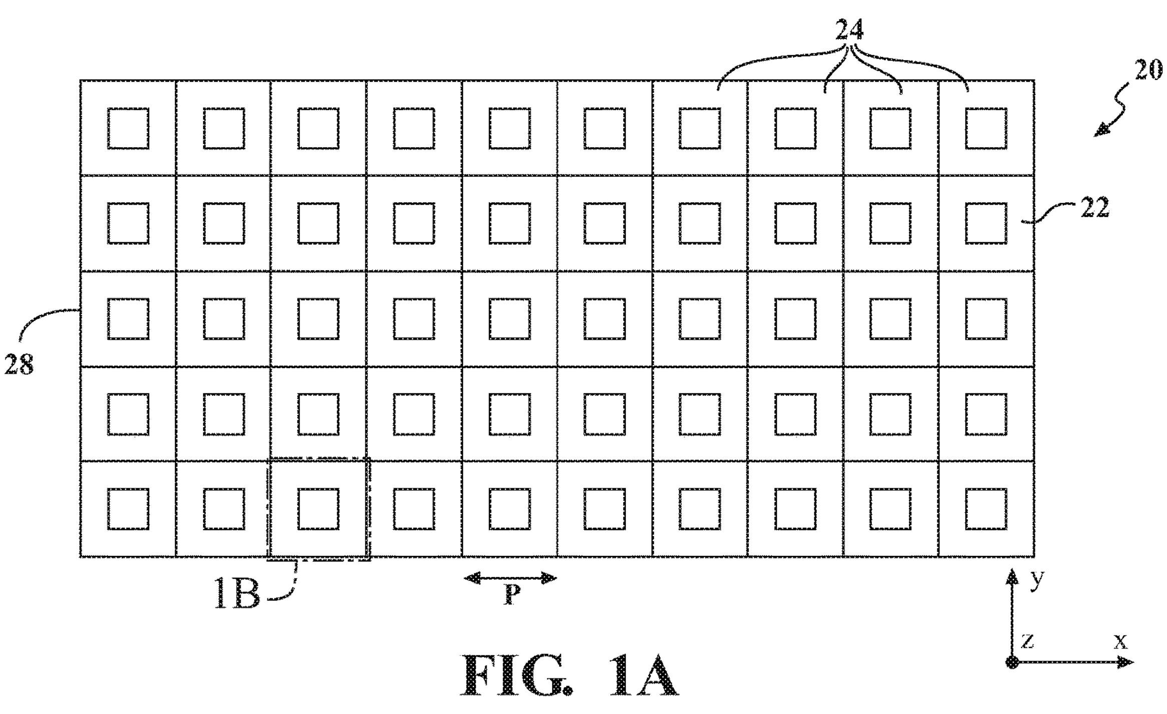
FIG. 1A
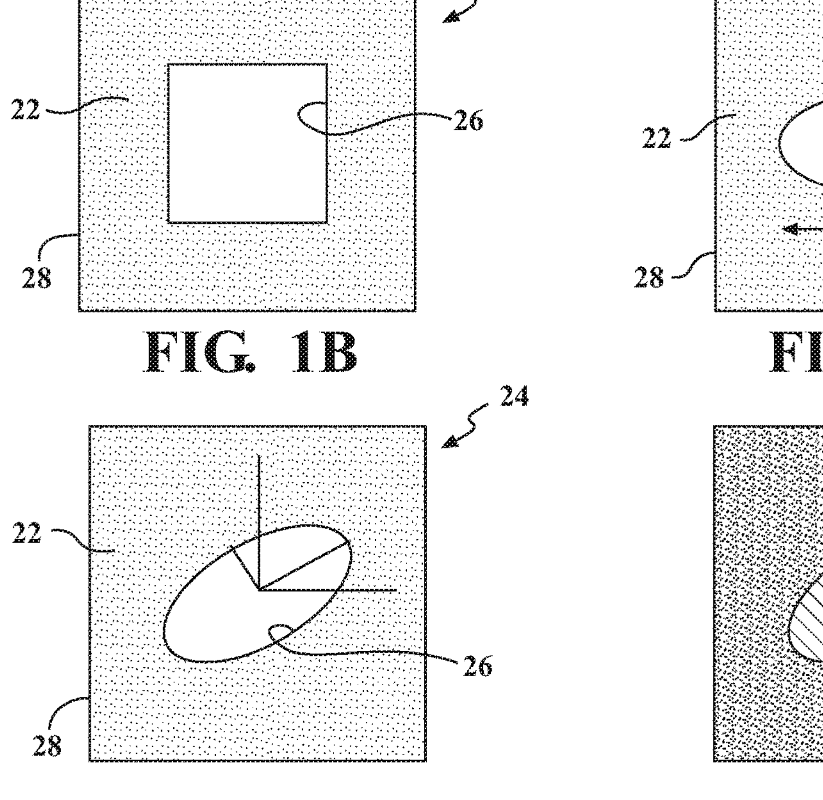
FIG. 1B
FIG. 2B
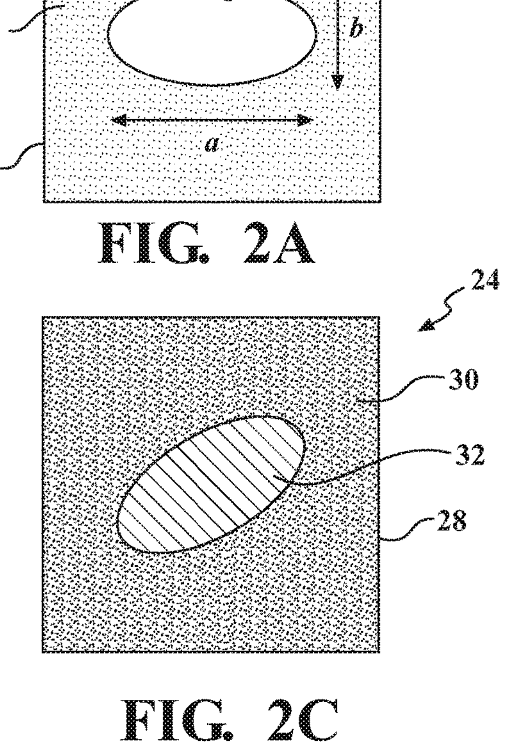
FIG. 2A
FIG. 2C

ANISOTROPIC ELASTIC METAMATERIALS

TECHNICAL FIELD

The present disclosure generally relates to designs and methods for making elastic materials and, more particularly, to anisotropic elastic metamaterials to control noise propagation, designed using topology optimization and reaction diffusion equations.

BACKGROUND

The background description provided herein is for the purpose of generally presenting the context of the disclosure. Work of the presently named inventors, to the extent it may be described in this background section, as well as aspects of the description that may not otherwise qualify as prior art at the time of filing, are neither expressly nor impliedly admitted as prior art against the present technology.

Elastic metamaterials are useful in controlling propagation of noise transmitted across elastic structures. With various acoustic devices, an elastic medium may be used in conjunction with another structural acoustic component. The elasticity of the combination may influence the shear wave conversion and propagation. Apertures, inclusions, pores, and various holes may be provided in the elastic medium for different acoustic designs. It is known that an orientation of such aperture, inclusion, pore, non-spherical hole, and the like, can affect a direction of elastic modulus. Thus, the orientation and size can be selected based on a desired elastic and acoustic response from the elastic medium. However, the local selection of the orientation and size of the aperture based on a desired acoustic response can be a complicated and resource-limited endeavor, especially with complex systems, shapes and customizations.

Accordingly, it would be desirable to provide improved, cost effective, and automated methods of designing elastic metamaterials that can be customized for various design considerations.

SUMMARY

This section provides a general summary of the disclosure and is not a comprehensive disclosure of its full scope or all of its features.

In various aspects, the present teachings provide a method for designing an elastic metamaterial for an acoustic radiator. The method includes defining an array of unit cells that form the acoustic radiator. The array includes an x-axis defining a longitudinal direction, a y-axis defining a transverse direction with respect to the x-axis, and a z-axis perpendicular to both the x-axis and the y-axis. The method includes determining a set of boundary conditions for a plurality of non-spherical apertures defined in an elastic medium, with each non-spherical aperture disposed within a boundary defined by a single respective unit cell of the array. The method may include using a gradient-based algorithm to optimize a porous media model domain for the elastic medium, where porosity is related to size dimensions of the non-spherical aperture and anisotropic elastic modulus is related to an angle of orientation of the non-spherical aperture. The method may include optimizing an objective function and obtaining a grayscale design that relates to the porosity and the anisotropic elastic modulus. Reaction diffusion equations may be used with the grayscale design to obtain a pattern for the non-spherical apertures. The method may include incorporating the pattern for the non-spherical apertures for the elastic medium coupled to each of the unit cells of the array.

In other aspects, the present teachings provide a method for manufacturing an elastic metamaterial. The method includes providing a layout of a continuous elastic medium including an array of unit cells and determining a set of boundary conditions for a plurality of non-spherical shapes to be defined in the elastic medium. The array may include an x-axis defining a longitudinal direction, a y-axis defining a transverse direction with respect to the x-axis, and a z-axis perpendicular to both the x-axis and the y-axis. The method includes designing a pattern for the continuous elastic medium having a plurality of non-spherical shapes. The method further includes using an additive manufacturing technique to create the continuous elastic medium such that each non-spherical shape is disposed within a boundary defined by a respective unit cell of the array. In various aspects, the step of designing the pattern for the elastic medium includes using a gradient-based algorithm to optimize a porous media model domain for the elastic medium. The porosity is related to size dimensions of the non-spherical aperture, and an anisotropic elastic modulus is related to an angle of orientation of the non-spherical aperture. The method may include optimizing an objective function and obtaining a grayscale design that relates to the porosity and anisotropic elastic modulus. Reaction diffusion equations may be used with the grayscale design to obtain the pattern for the non-spherical apertures. In various aspects, the manufacturing may include using a multi-material additive manufacturing technique to create the continuous elastic metamaterial, with the elastic medium formed with a first material having a first stiffness, and with the non-spherical shape formed with a second material different from the first material and having a second stiffness, less than the first stiffness. In other aspects, the non-spherical shape is provided as a non-spherical aperture defined in the elastic medium.

In still other aspects, the present teachings provide an elastic metamaterial having a continuous elastic medium including an array of unit cells and defining a pattern of non-spherical shapes. Each non-spherical shape is disposed within a boundary defined by each respective unit cell. A size and angle of orientation of each non-spherical shape is designed using a gradient-based algorithm to provide a grayscale design. Reaction diffusion equations may be used with the grayscale design to obtain the pattern for the non-spherical shapes. In various aspects, the gradient-based algorithm includes a topology optimization problem solved according to constitutive laws associated with a linearly elastic medium. In various aspects, the non-spherical shape is provided as a non-spherical aperture defined in the elastic medium. In other aspects, the non-spherical shape may be provided as a different material from the remainder of the elastic medium. For example, the continuous elastic medium may be made with a first material having a first stiffness, and the non-spherical shape is provided with a second material different from the first material and having a second stiffness less than the first stiffness.

Further areas of applicability and various methods of enhancing the above technology will become apparent from the description provided herein. The description and specific examples in this summary are intended for purposes of illustration only and are not intended to limit the scope of the present disclosure.

BRIEF DESCRIPTION OF THE DRAWINGS

The present teachings will become more fully understood from the detailed description and the accompanying drawings, wherein:

FIG. 1A generally illustrates a shape of an exemplary elastic metamaterial of the present technology, provided as an acoustic radiator or partition component that includes an elastic medium with a plurality of unit cells arranged in an array;

FIG. 1B is a magnified schematic representation of a single unit cell of the acoustic radiator of FIG. 1A, and illustrates a non-spherical aperture defined in the elastic medium;

FIGS. 2A-2C provide examples of the dimension and orientation variables of additional unit cells having a non-spherical aperture (FIGS. 2A and 2B) and a non-spherical shape (FIG. 2C);

Figure 3A:
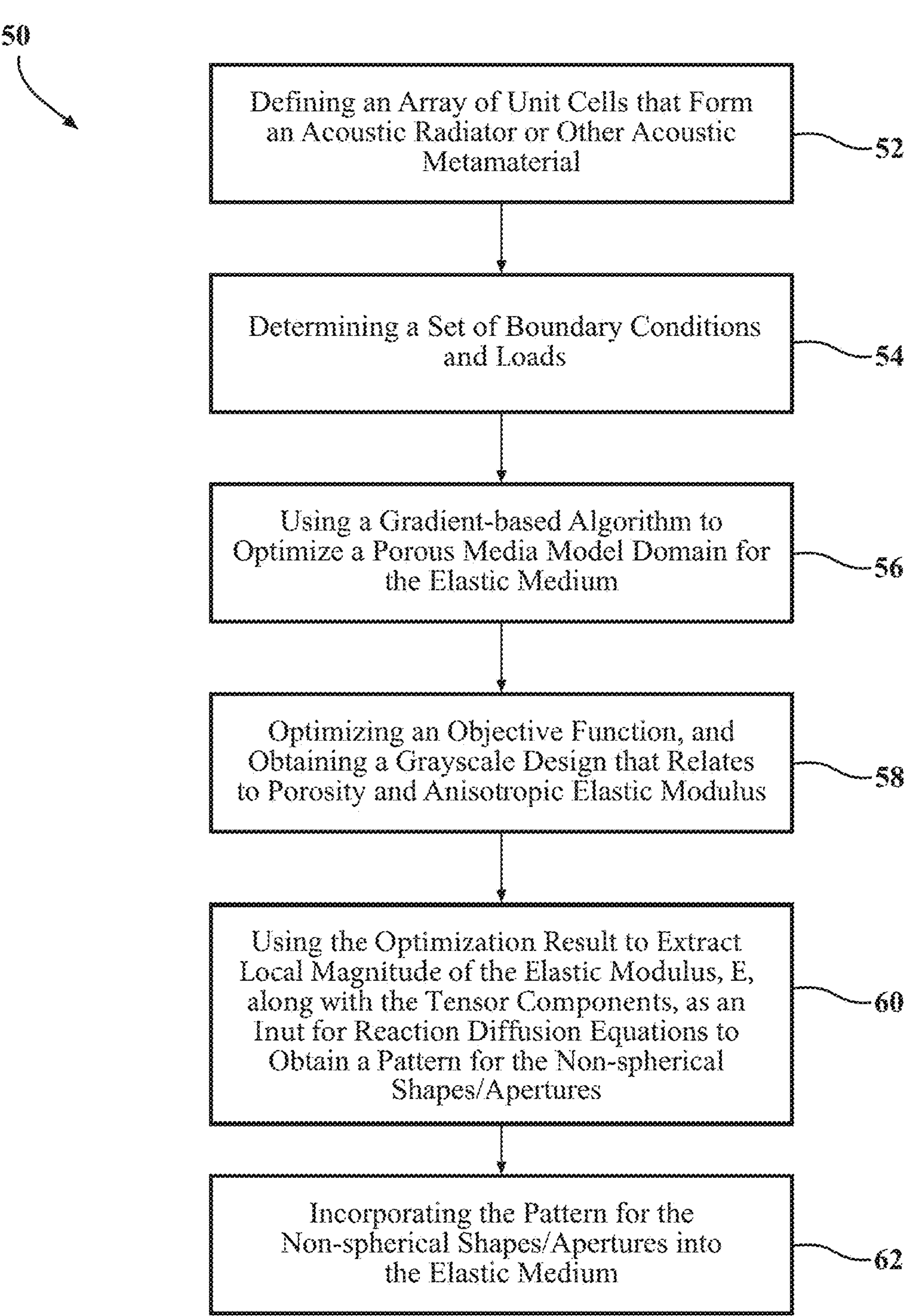
FIG. 3A is an exemplary method flow chart for designing a pattern of the size and orientation of the non-spherical apertures according to various aspects of the present technology.

It should be noted that the figures set forth herein are intended to exemplify the general characteristics of the methods, algorithms, and devices among those of the present technology, for the purpose of the description of certain aspects. These figures may not precisely reflect the characteristics of any given aspect and are not necessarily intended to define or limit specific embodiments within the scope of this technology. Further, certain aspects may incorporate features from a combination of figures.

DETAILED DESCRIPTION

The present technology generally provides elastic metamaterials with an elastic medium that can be customized as an array of unit cells with non-spherical shapes and/or non-spherical apertures in order to control acoustic waves. In various aspects, the elastic metamaterials can be used in the design of devices such as acoustic radiators, acoustic partitions, and the like, ultimately where an acoustic response is influenced by the properties of the elastic medium, in particular, influenced by differences in the elastic modulus. As an acoustic partition, the elastic metamaterial can be provided with a customized interior layout/structure for directing sound in a predefined manner. For example, non-spherical apertures, inclusions, pores, various holes, as well as shaped portions provided with a different material or thickness (having a different stiffness) may be provided in a spatial design in the elastic medium in order to obtain different elastic and acoustic properties. The size and orientation of such non-spherical aperture, inclusion, pore, hole, shaped portion and the like, can affect a direction of elastic modulus of the elastic medium. The orientation can be designed and/or selected based on an elastic and acoustic response from the elastic medium. In various examples, an acoustic radiator can be designed for redirecting sound and controlling sound waves, where the elastic medium may be configured for use with elastic wave guiding functionality. For example, when a sound wave engages one side of an acoustic radiator, the elastic properties of the elastic medium modifies how energy is transmitted to the other side, and thus modifies the acoustic response on the other side of the acoustic radiator structure. It is also contemplated that the present technology may provide certain uses related to acoustic cloaking.

More specifically, the present technology provides new techniques and methods useful for the design and selection of the size and orientation of non-spherical shapes and/or non-spherical apertures in the elastic medium that can be tailored to and/or based on a desired acoustic response. In this regard, the present technology provides for the use of reaction diffusion equations in a post-processing technique that can be used to determine and develop a pattern for an elastic medium having local microstructures, for example, with each local microstructure being provided as non-spherical shape having a different stiffness. This results in the design of a pattern of non-spherical shapes/apertures in the elastic medium. The elastic medium may then be coordinated with an array of unit cells, for example, where each non-spherical shape/aperture is located within a boundary defined by a single unit cell of the array.

FIG. 1A illustrates an exemplary acoustic radiator 20, also referred to as an acoustic partition, which includes an elastic medium 22 having a plurality of unit cells 24. In various aspects, the unit cells 24 are connected and the elastic medium 22 may be a continuous medium. As shown, the unit cells 24 are provided as an array with an organized series or arrangement. The array has an x-axis defining a longitudinal direction, a y-axis defining a transverse direction with respect to the x-axis, and a z-axis that is perpendicular to both the x-axis and the y-axis. The specific shape, orientation, and design of the array, as well as the acoustic radiator 20 itself, may vary based on the desired acoustic response and the ultimate intended location where the acoustic radiator 20 will be used. If desired, the acoustic radiator may optionally be provided as a periodic array, having a period, P.

FIG. 1B is a magnified schematic representation of a single unit cell 24 of the acoustic radiator 20 of FIG. 1A and illustrates a non-spherical shape 26 defined in the elastic medium 22. A non-spherical shape provides an anisotropic elastic modulus ($G_x \neq G_y$). The non-spherical shape 26 in FIG. 1B is specifically provided as an aperture in the elastic medium 22. In various other aspects, the non-spherical shape can be provided as a shaped region made of a different material from the elastic medium 22, or a region having the same material of the elastic medium, but provided having a different thickness (in the z-axis), such that it exhibits a different stiffness and compliance. The non-spherical aperture 26 is defined in the elastic medium 22 and located within a boundary 28, or perimeter, defined by the respective unit cell 24. It should be understood that the boundary 28 of each unit cell 24 need not be physically delineated in the acoustic radiator 20, and the boundaries 28 of the unit cells 24 are only shown in the figures for explanatory purposes. Additionally, the features of the non-spherical shape/aperture may vary from one unit cell to another unit cell. As mentioned above, both the size and orientation of the non-spherical shapes/apertures 26 are important design considerations because they influence the direction of the elastic modulus of the elastic medium 22. The frequency response is related to the local material design. As will be discussed below, at a specific vibratory frequency, top side RMS velocity and acoustic radiation are proportional to the transverse spectral displacement.

The exemplary array of unit cells 24 provided in FIG. 1A is shown as a generally rectangular shape with a series of columns and rows of unit cells 24 each having a square shaped boundary 28 such that dimensions in the x-axis and y-axis are equal or substantially equal. As used herein, an elastic medium can broadly include a solid phase material (distinguished from a liquid or gas phase) that can change its shape as a result of exposure to a deforming strain, force or load, and where the elastic modulus is a measurement of the elastic medium's resistance to being elastically deformed in response to an applied stress, such as an acoustic wave.

FIGS. 2A and 2B provide examples of the dimension and orientation variables of unit cells 24 having a non-spherical shape 26, specifically provided as an oval shape. While the non-spherical shape 26 defined in the unit cell 24 of FIGS. 2A and 2B is provided as an aperture (filled with air), in other aspects, the shape can be occupied by a different material having a different stiffness, or it can be the same elastic material as the remainder of the unit cell, but thinner. The materials and compositions useful with the present technology are not meant to be limiting, and can include various polymers, polymer-based materials, metals, composite materials, and the like that are suitable for acoustic use. As shown in FIG. 2C, one or more unit cells 24 of the array may be provided made of two materials, a stiffer material 30 and softer material 32 as the non-spherical shape. In one example, the stiffer material 30 can be a rigid polymer or metal and then softer material 32 can be a softer polymer, or a thinner material. It should be understood that in certain aspects, the stiffer and softer materials could be reversed. In another aspect, the materials within the array itself can be varied or functionally graded from one unit cell to another unit cell, providing materials with a different compliance for the stiffer material, and a different compliance for softer material. The different elastic properties of the different materials will affect the vibration response and how the sound wave propagates on the other side of the acoustic radiator. For example, the frequency response of the acoustic radiator may be based on a single-material or multi-material selection design of the acoustic radiator. FIG. 2A illustrates the non-spherical aperture 26 having two unit cell variables a width dimension, a, along the x-axis and a height dimension, b, along the y-axis. FIG. 2B provides an orientation angle, Θ, that varies the orientation of the non-spherical aperture 26.

Figure 3B:
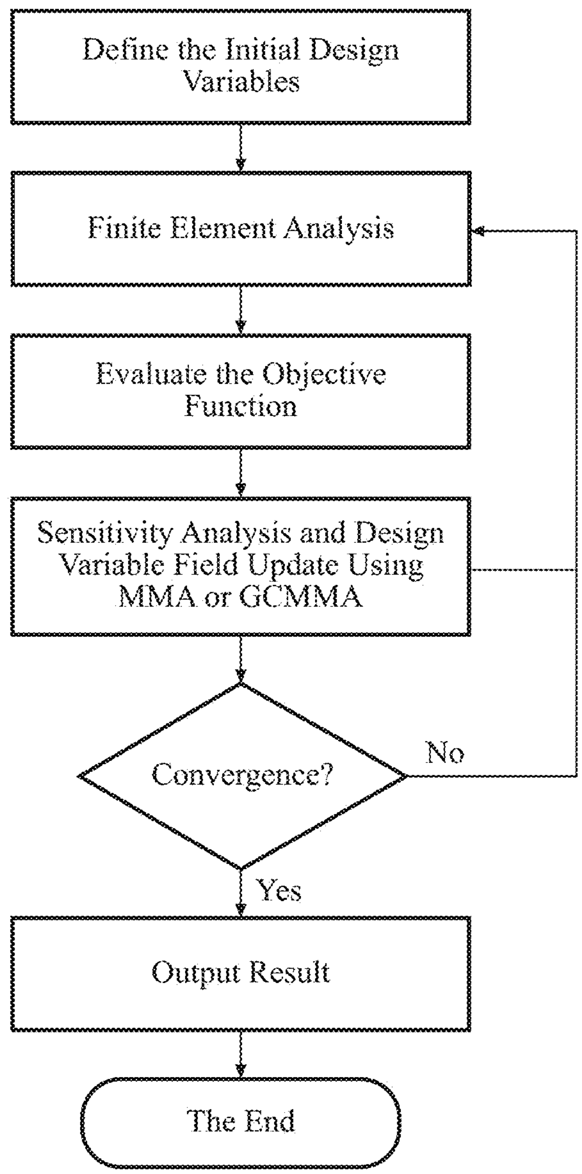
FIG. 3B is a flowchart of an exemplary gradient based algorithm using method of moving asymptotes (MMA) or globally convergent method of moving asymptotes (GCMMA) to optimize the porous media model domain.

FIG. 3A is an exemplary flow chart with a method 50 for designing a pattern of the size and orientation of the non-spherical shapes/apertures according to various aspects of the present technology. With reference to step 52, the method includes generally defining an array of unit cells that collectively form an acoustic radiator, or other elastic metamaterial. In this step, elastic modulus tensor component material mappings may be created, such as 3-D maps, that relate unit cell elastic properties to specific hole sizes and orientations. These maps (not shown) may be constructed in a non-limiting example such that the x-axis is the unit cell hole size, the y-axis is the orientation angle for the hole, and the z-axis is the value of an elastic modulus tensor component (E11, E12, or E22). For different unit cell designs, different 3-D maps may be created where the associated elastic properties allow for one to reconstruct a structure configuration using associated grayscale information. With reference to step 54, the method includes the feature of determining a set of boundary conditions and loads for the acoustic radiator that includes a plurality of non-spherical shapes/apertures defined in the elastic medium. As described herein, each non-spherical shape/aperture is intended to be located or disposed within the boundary 28 defined by a single respective unit cell 24 of the array. With reference to method step 56, the method may include using a gradient-based algorithm to optimize a porous media model domain for the elastic medium utilizing the material property mappings from step 52, where porosity is related to size dimensions of the non-spherical shape/aperture and anisotropic elastic modulus is related to an angle of orientation of the non-spherical shape/aperture. FIG. 3B is a flowchart with additional details of an exemplary gradient-based algorithm using method of moving asymptotes (MMA) optimizer or globally convergent method of moving asymptotes (GCMMA) optimizer to optimize the porous media model domain using a topology optimization problem, discussed in more detail below. The method may include optimizing an objective function and obtaining a grayscale design that relates to the porosity and the anisotropic elastic modulus, as provided in method step 58. With reference to method step 60, reaction diffusion equations may be used to de-homogenize the grayscale design, again utilizing the mapped material property to structure relationships, to obtain a pattern for the non-spherical shapes/apertures. Lastly, with reference to method step 62, the method may include incorporating the pattern for the non-spherical shapes/apertures for the elastic medium.

With renewed reference to method steps 52 and 54, and with respect to the features of determining a set of boundary conditions for the plurality of non-spherical shapes/apertures defined in the elastic medium, in various aspects, the methods may include using at least one look-up table that provides a mapping of grayscale design information and unit cell designs to a size and orientation of the non-spherical shapes/apertures. In certain aspects, in addition to, or as an alternative to data provided in look-up tables, the data may be provided as a three-dimensional surface mapping to bound the range of permissible values. For example, the x-axis of the mapping corresponds to the width dimension of the non-spherical shape/aperture in the unit cell, the y-axis corresponds to the height dimension of the non-spherical shape/aperture, and the z-axis is representative of the elastic modulus tensor component. In various aspects, the at least one look-up table may be based on data obtained from varying the width dimension, a (x-axis), and height dimension, b (y-axis), of the non-spherical shape/aperture in the unit cell over a range of values, and calculating the tensor component (z-axis). For example, s standard coordinate transformation can be used to find the elasticity components in a rotated coordinate system. Maps can be built for the homogenized values. The initial inputs for certain of the boundary and geometry data useful with the present technology may be explicit or implicit, or a combination of both; in certain instances, at least a portion of the data may be estimated.

With renewed reference to method step 56, and with respect to the gradient based algorithm, in various aspects, the algorithm includes a topology optimization problem that may be solved according to one of the constitutive laws associated with a linearly elastic medium. With reference to FIGS. 2A and 2B, three spatial design variables can be defined, including the orientation angle, Θ, that is determined by optimized angle information, and the width and height a, b, determined from a porosity of a grayscale field. The topology optimization problem may be solved by maximizing or minimizing a spectral displacement variable, or set of variables, of the elastic medium for a given objective function. The spectral displacement variable may be proportional to velocity at one or both of a predetermined point (or set of points) and a predetermined frequency. The frequency response is related to the local material design. For example, with a frequency response analysis, governing equations are provided for an elastic body as a dynamic system and solved for in the frequency domain. For a time domain analysis, an equation of motion in a linear elastic medium may be useful. Elastic waves and may exhibit various phenomena, including, but not limited to, diffraction, reflection, and interference. In various aspects, the equation of motion in a linear elastic medium solved in the frequency domain may be written as:

$$-\rho\omega^2 u=\nabla\cdot(C:\varepsilon)+F_v e^{i\varphi};\ \varepsilon=\tfrac{1}{2}[(\nabla u)^T+\nabla u]$$

where u is the displacement vector, ρ is the material density, co is the frequency, C is the fourth-order elasticity tensor which is a function of the material Young's modulus (E) and Poisson's ratio (υ), and $F_v$ is the volumetric force. The presence of an elastic medium can influence the acoustic velocity, which generally increases with the stiffness of a material and decreases with the density of a material. For the purposes of the present technology, the stiffness represents a resistance of the elastic medium to deformation by an applied force.

In various aspects, once a porous media model domain for the elastic medium is optimized, and a grayscale design is developed relating to porosity and anisotropic elastic modulus, the novel pattern for the non-spherical shapes/apertures of the present technology may be generated based, in part, on a Turing pattern from reaction diffusion equations. In various aspects, the reaction diffusion equations are used in what may be referred to as a post-processing routine, with the grayscale design and optimized anisotropic Young's modulus distribution, to obtain a pattern for the non-spherical shapes/apertures. The use of the reaction diffusion equations enables an extraction of the local magnitude of the elastic modulus, in addition to the tensor components. For example, the GS reaction diffusion equations may be used with the grayscale design to obtain a pattern of non-spherical shapes/apertures using an extracted unit cell porosity magnitude plus a tensor-expression of the anisotropic elastic modulus. In various aspects, the methods of the present technology may repeatedly solve the reaction diffusion equations for some time period, and in certain instances, may switch the anisotropy strength using at least two sets of diffusion tensors. The extractions from the reaction diffusion equations results from obtaining a scalar field. The output pattern is a distribution of high scalar values and low scalar values, similar to monochrome image data where a high value is black, and a low value is gray.

As is known in the art, reaction-diffusion systems are mathematical models that correspond to physical phenomena. In one example, a change in space and time of the concentration of one or more chemical substances is modeled. In mathematical terms, reaction-diffusion systems generally take the form of semi-linear parabolic partial differential equations represented by the general form as follows:

$$\partial_t q=\underline{\underline{D}}\nabla^2 q+R(q)$$

where q(x, t) represents the unknown vector function, D is a diagonal matrix of diffusion coefficients, and R accounts for all local reactions. Reaction and diffusion of chemical species can produce a variety of patterns, reminiscent of those often seen in nature. An example of such a reaction is generally provided as follows:

$$\frac{\partial u}{\partial t}=D_u\nabla^2 u-uv^2+F(1-u),$$

$$\frac{\partial v}{\partial t}=D_v\nabla^2 v+uv^2-(F+k)v.$$

The partial differential equations modeling this process may be simulated with a variety of numerical techniques. In various aspects, good results can be obtained using methods such as forward Euler integration of the finite-difference equations that one obtains by spatial discretization of the Laplacian, or the diffusion coefficients can be estimated for a target design variable.

The reaction diffusion model is one exemplary mathematical model that describes the behavior of two chemical substances, and calculates the concentration of the two substances at a given time based upon the substances diffusion, feed rate, removal rate, and a reaction between the two. This simulation not only models the underlying process of a chemical reaction but can also result in patterns of the substances that are remarkably similar to patterns found in nature. Examples include patterns on animals, such as stripes on zebras, a leopard's skin, spots on butterflies, patterns on fish; fingerprints; ripples on sand; patterns of veins on a leaf; and various other biological phenomena. With the present technology, certain of the patterns resulting from this model can be used for the design of non-spherical shape/aperture and its orientation.

To illustrate the model, one analogy presented is to imagine an area or space containing various concentrations of each chemical substance U and V at time zero. Over time, substance U is fed into the reaction at a given rate, while substance V is removed at a given rate. Further, two molecules of V can react with one of U, which converts the substance of U to V as follows:

$$U+2V\rightarrow 3V$$

$$v\rightarrow P$$

U, V, and P are chemical substances. A simulation is accomplished using the two partial differential equations listed above, each representing the change in concentration of a substance over time, where u and v are independent variables that represent their respective concentrations; $D_u$ and $D_v$ are their respective diffusion rates or diffusion tensors, which can be calculated from permeability. The parameter k represents the rate of conversion of V to P; and F represents the rate of process that feeds U and drains U, V, and P. The parameters k and F are arbitrary positive numbers that can be adjusted. Each diffusion tensor is generally a 3×3 matrix reflecting diffusion rates in different directions.

The change in u (upper partial differential equation) is dependent upon its reaction with v (hence the subtraction (−) of $uv^2$) and is fed at a certain rate (+F, scaled to its current concentration). The change in v (lower partial differential equation) is dependent upon its reaction with u (hence the addition (+) of $uv^2$), and is removed at a given rate (−k, scaled by the feed rate and concentration of V). The concentration of U or V at each position is updated at each time increment (typically 1) based upon the result of the corresponding equation. The values for the feed rate, removal rate, and diffusion rate are entered into the equations. For example, on a 2D grid, the Laplacian Operator could be calculated on a convolution matrix. To calculate the new concentration, the current concentration and each surrounding concentration is multiplied by the corresponding value in the matrix (where the current position corresponds to the center position in the convolution matrix) and all values summed. This value technically represents the difference in concentrations between the current position and the surrounding positions.

The above model can be programmed in a suitable computer code as is known in the art. In various aspects, the resulting model provides an image representing the reaction container, with each point or pixel of the image representing the concentration of V (v) at that position. For example, the reaction diffusion equations can be solved with various numerical methods, such as the finite differential method or the finite element method. The initial value of u and v could be random noise distribution. By solving the equations for some time period with an appropriate parameter set, a steady state is obtained. Then, one can extract the local magnitude of the elastic modulus and the tensor components in order to create the pattern for the non-spherical shapes/apertures.

With respect to the manufacturing of the elastic metamaterials of the present technology, additive manufacturing is a technique useful herein to create a three-dimensional component by aligning and/or depositing overlapping layers of materials under the guided control of a computerized or programmed device. The present technology generally teaches methods for the manufacture of elastic metamaterials that may include multi-material additive manufacturing techniques. The methods begin as described above and include providing a layout of an elastic medium including an array of unit cells and determining a set of boundary conditions for a plurality of non-spherical shapes to be defined in the elastic medium. The array may include an x-axis defining a longitudinal direction, a y-axis defining a transverse direction with respect to the x-axis, and a z-axis perpendicular to both the x-axis and the y-axis. The method includes designing a pattern for the elastic medium having a plurality of non-spherical shapes. The method further includes using an additive manufacturing technique to create the elastic medium such that each non-spherical shape is disposed within a boundary defined by a respective unit cell of the array. In various aspects, the step of designing the pattern for the elastic medium includes using a gradient-based algorithm to optimize a porous media model domain for the elastic medium. The porosity is related to size dimensions of the non-spherical aperture, and an anisotropic elastic modulus is related to an angle of orientation of the non-spherical aperture. As discussed above, the method may include optimizing an objective function, and obtaining a grayscale design that relates to the porosity and anisotropic elastic modulus. Reaction diffusion equations may be used with the grayscale design to obtain the pattern for the non-spherical apertures. In various aspects, the manufacturing may include using a multi-material additive manufacturing technique to create the elastic metamaterial, with the elastic medium formed with a first material having a first stiffness, and with the non-spherical shape formed with a second material different from the first material and having a second stiffness, less than the first stiffness. In other aspects, the non-spherical shape may be provided as a non-spherical aperture defined in the elastic medium.

It should be understood that while various methods are described herein using 2D examples, in other methods the present technology is readily extendable to 3D. For various 3D manufacturing techniques, cubic unit cells can be designed and provided with inclusions that may be ellipsoidal or of other geometric shape that is readily parameterized and can likewise be optimized in a manner similar to the 2D examples described herein.

Examples

Figure 4A:
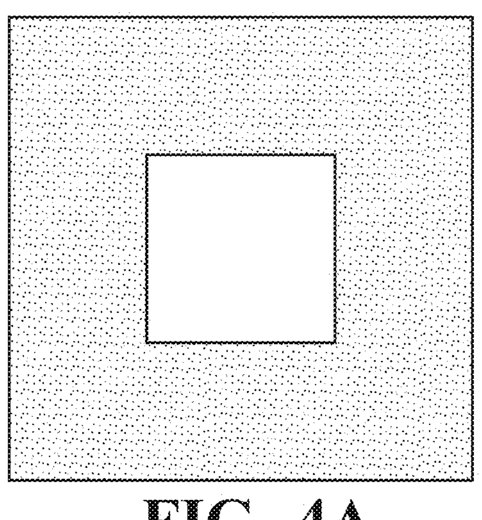
FIGS. 4A-4E provide additional examples of shapes, sizes, and orientations of non-spherical shapes/apertures.
Figure 4B:
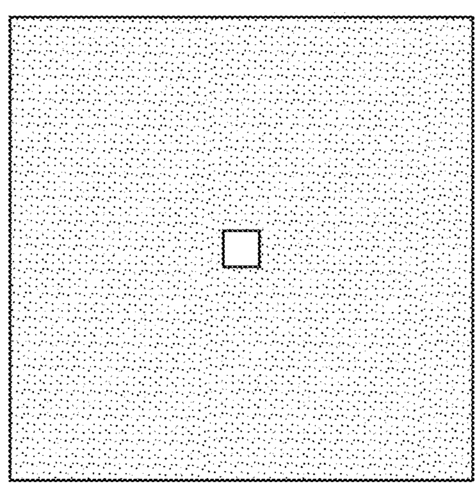
Figure 4C:
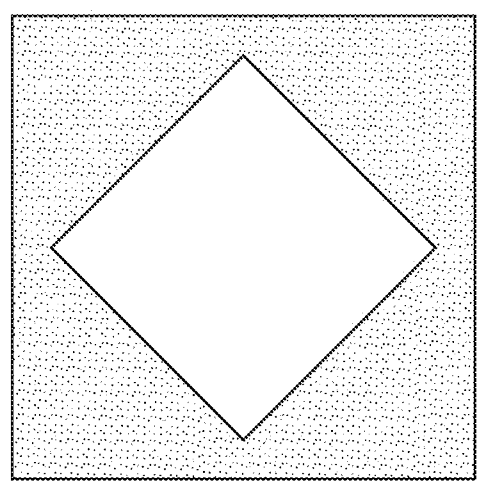
Figure 4D:
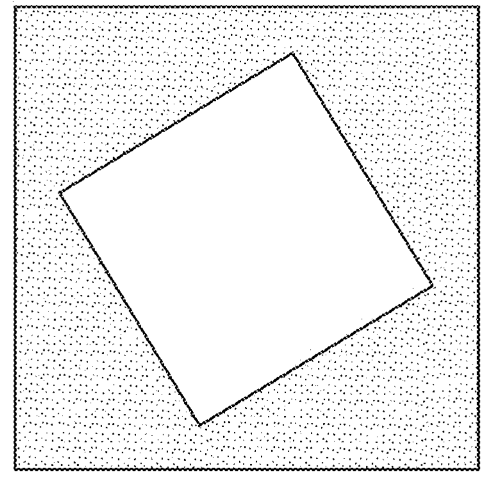
Figure 4E:
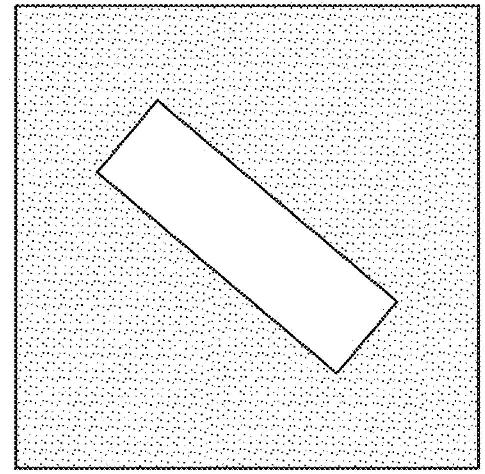

FIGS. 4A-4E provide additional examples of shapes, sizes, and orientations of non-spherical shapes/apertures. With reference to FIGS. 4A and 4B, the difference in the shape/aperture size for each example may be determined from the grayscale field. For example, the size is related to the magnitude of the elastic modulus. With reference to FIGS. 4C-4E, the shape/aperture orientation is related to the local anisotropic elasticity in the optimization formulation.

To further understand the methods of the present technology, FIGS. 5-8 provide additional illustrations of different designs of the elastic metamaterials (similar to FIG. 1) provided with representative data of the structure top side root mean square (RMS) velocity vs. the frequency. In optimizing the designs, one goal is to minimize the transverse spectral displacement (or RMS velocity) of either the entire or some portion of the top side of the acoustic structure.

Figure 5A:
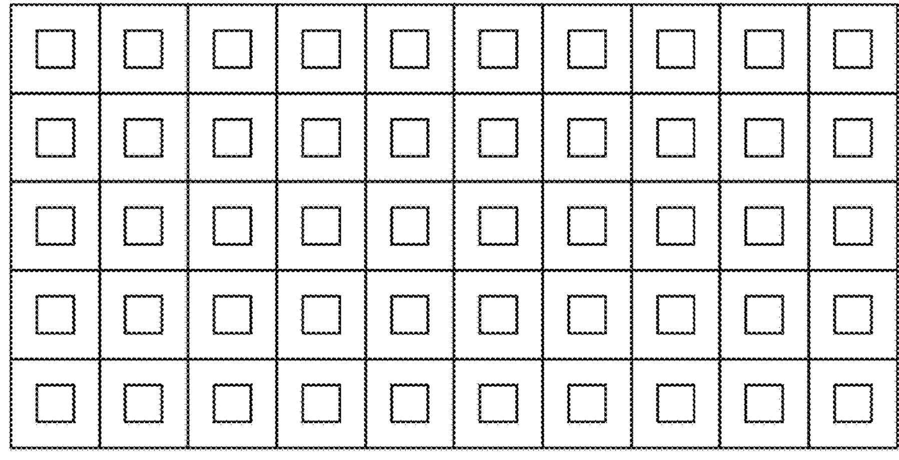
FIGS. 5A-5C provide a schematic illustration of a first acoustic radiator with fixed boundary conditions, an associated plot of the structure top side root mean square (RMS) velocity vs. the frequency, and a mode shape of a structure including a pattern of non-spherical shapes/apertures.
Figure 5A:
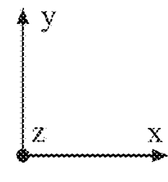
Figure 5B:
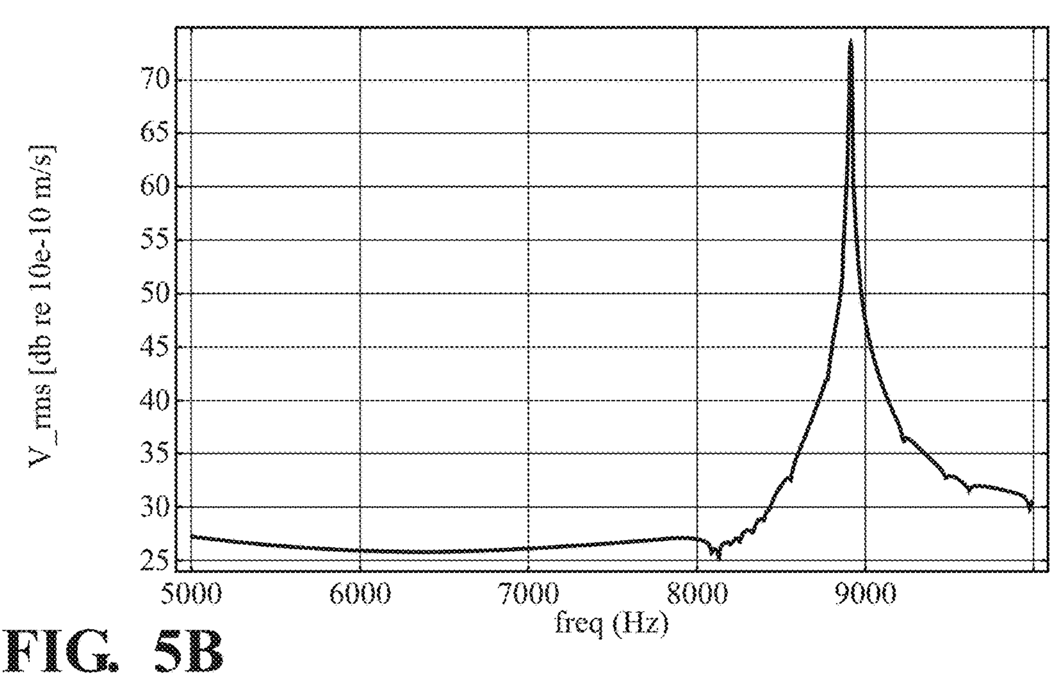
Figure 5C:
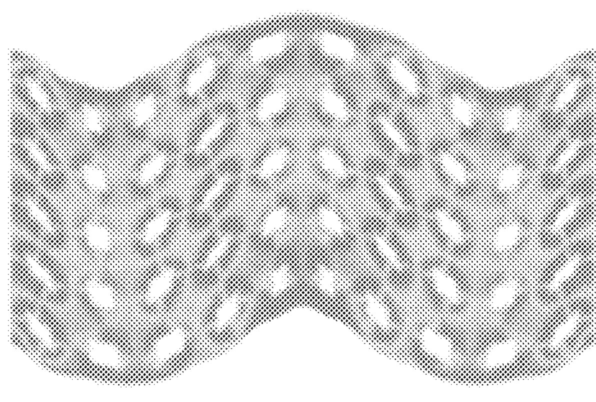

FIGS. 5A-5C respectively provide a schematic illustration of a first acoustic radiator with fixed boundary conditions (FIG. 5A), an associated plot of the structure top side RMS velocity vs. the frequency (FIG. 5B), and a mode shape of the structure including a pattern of non-spherical shapes/apertures at a frequency of about 8900 Hz (FIG. 5C).

Figure 6A:
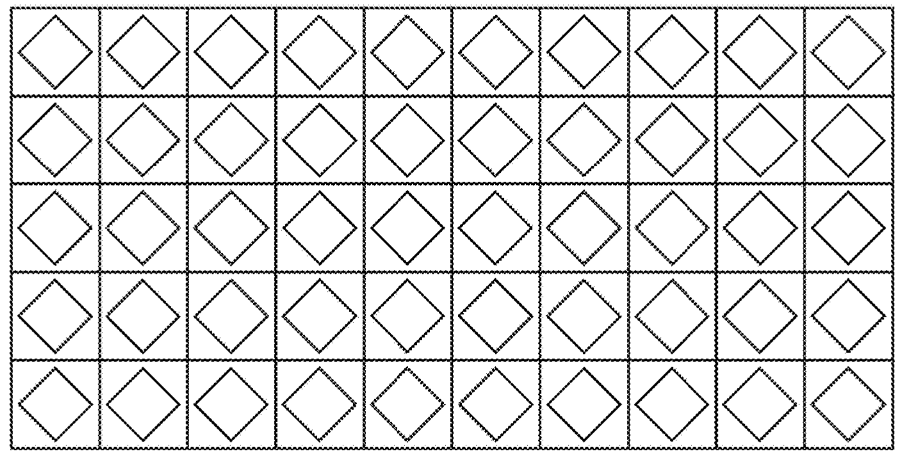
FIGS. 6A-6C provide a schematic illustration of a second acoustic radiator, an associated plot of the structure top side RMS velocity vs. the frequency, and a mode shape of a structure including a pattern of non-spherical shapes/apertures.
Figure 6A:
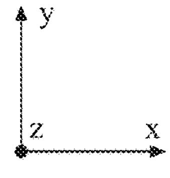
Figure 6B:
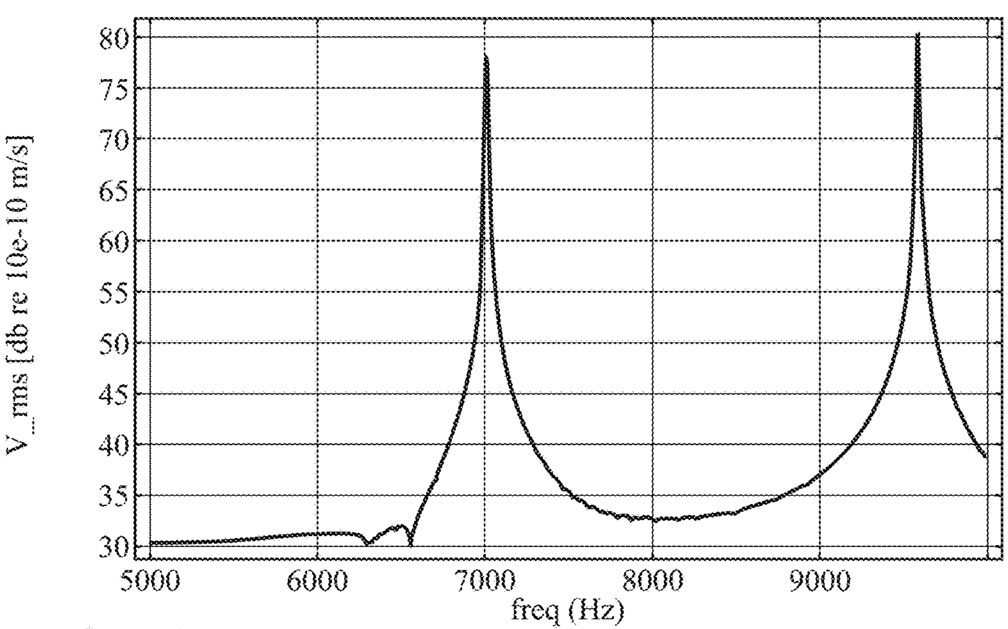
Figure 6C:
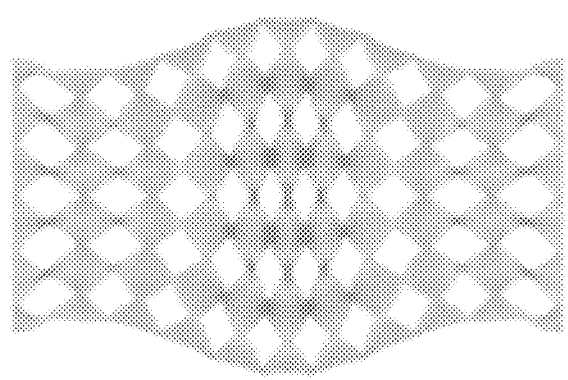

FIGS. 6A-6C respectively provide a schematic illustration of a second acoustic radiator (FIG. 6A), an associated plot of the structure top side RMS velocity vs. the frequency (FIG. 6B), and a mode shape of the structure including a pattern of non-spherical shapes/apertures at a frequency of about 9600 Hz (FIG. 6C).

Figure 7A:
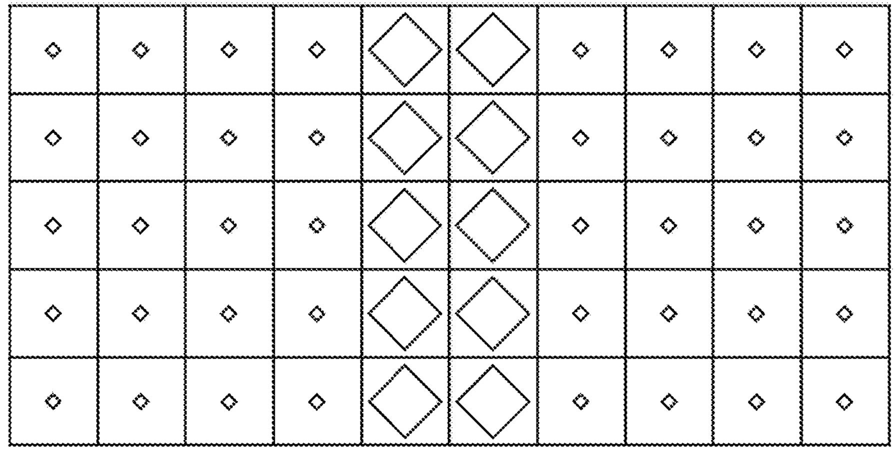
FIGS. 7A-7C provide a schematic illustration of a third acoustic radiator, an associated plot of the structure top side RMS velocity vs. the frequency, and a mode shape of a structure including a pattern of non-spherical shapes/apertures.
Figure 7A:
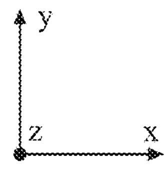
Figure 7B:
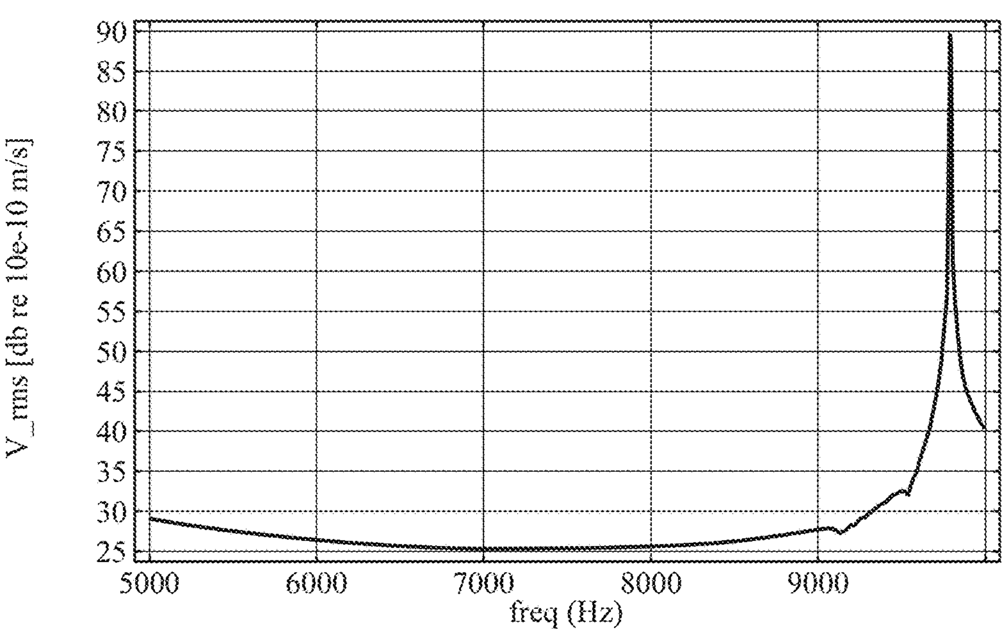
Figure 7C:
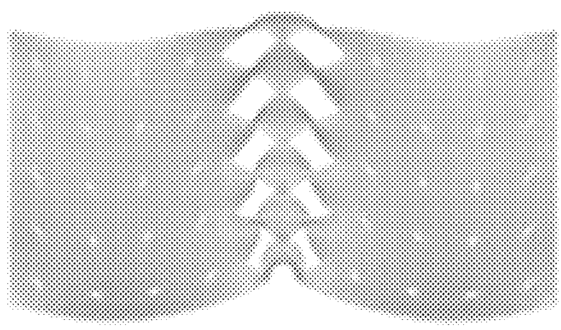

FIGS. 7A-7C respectively provide a schematic illustration of a third acoustic radiator (FIG. 7A), an associated plot of the structure top side RMS velocity vs. the frequency (FIG. 7B), and a mode shape of the structure including a pattern of non-spherical shapes/apertures at a frequency of about 9700 Hz (FIG. 7C).

Figure 8A:
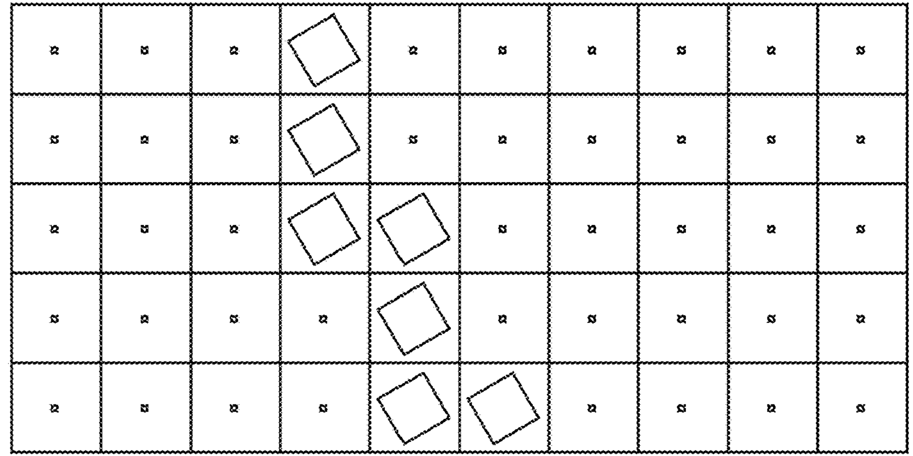
FIGS. 8A-8C provide a schematic illustration of a fourth acoustic radiator, an associated plot of the structure top side RMS velocity vs. the frequency, and a mode shape of a structure including a pattern of non-spherical shapes/apertures.
Figure 8A:
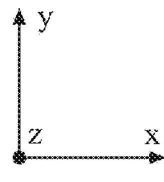
Figure 8B:
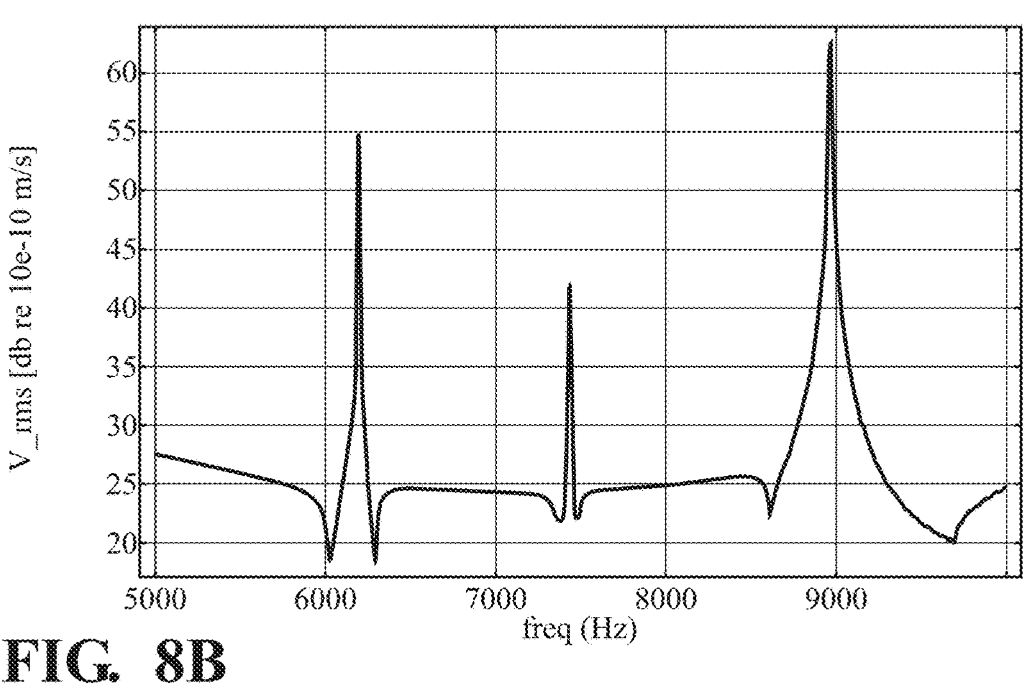
Figure 8C:
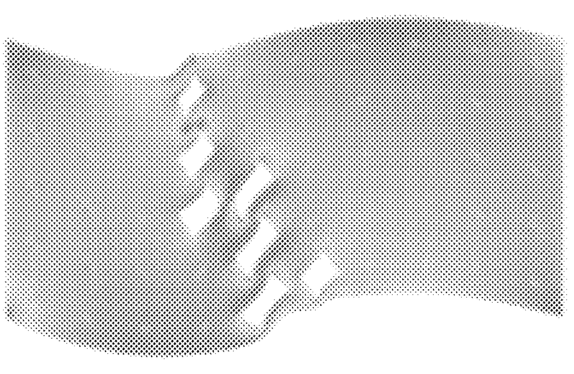

FIGS. 8A-8C respectively provide a schematic illustration of a fourth acoustic radiator (FIG. 8A), an associated plot of the structure top side RMS velocity vs. the frequency (FIG. 8B), and a mode shape of the structure including a pattern of non-spherical shapes/apertures at a frequency of about 6200 Hz (FIG. 8C).

The foregoing description is provided for purposes of illustration and description and is in no way intended to limit the disclosure, its application, or uses. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations should not be regarded as a departure from the disclosure, and all such modifications are intended to be included within the scope of the disclosure.

As used herein, the phrase at least one of A, B, and C should be construed to mean a logical (A or B or C), using a non-exclusive logical "or." It should be understood that the various steps within a method may be executed in different order without altering the principles of the present disclosure. Disclosure of ranges includes disclosure of all ranges and subdivided ranges within the entire range, including the endpoints.

The headings (such as "Background" and "Summary") and sub-headings used herein are intended only for general organization of topics within the present disclosure, and are not intended to limit the disclosure of the technology or any aspect thereof. The recitation of multiple embodiments having stated features is not intended to exclude other embodiments having additional features, or other embodiments incorporating different combinations of the stated features.

As used herein, the terms "comprise" and "include" and their variants are intended to be non-limiting, such that recitation of items in succession or a list is not to the exclusion of other like items that may also be useful in the devices and methods of this technology. Similarly, the terms "can" and "may" and their variants are intended to be non-limiting, such that recitation that an embodiment can or may comprise certain elements or features does not exclude other embodiments of the present technology that do not contain those elements or features.

The broad teachings of the present disclosure can be implemented in a variety of forms. Therefore, while this disclosure includes particular examples, the true scope of the disclosure should not be so limited since other modifications will become apparent to the skilled practitioner upon a study of the specification and the following claims. Reference herein to one aspect, or various aspects means that a particular feature, structure, or characteristic described in connection with an embodiment or particular system is included in at least one embodiment or aspect. The appearances of the phrase "in one aspect" (or variations thereof) are not necessarily referring to the same aspect or embodiment. It should be also understood that the various method steps discussed herein do not have to be carried out in the same order as depicted, and not each method step is required in each aspect or embodiment.

What is claimed is:

1. A method for manufacturing an elastic metamaterial for an acoustic radiator, the method comprising:

defining an array of unit cells that form the acoustic radiator, the array including an elastic medium comprising a solid phase material;

determining a set of boundary conditions for a plurality of non-spherical apertures defined in the elastic medium of the array, with each non-spherical aperture disposed within a boundary defined by a single respective unit cell of the array;

using a gradient-based algorithm to optimize a porous media model domain for the elastic medium, where porosity is related to size dimensions of the plurality of non-spherical apertures and an anisotropic elastic modulus is related to an angle of orientation of the non-spherical aperture;

optimizing an objective function, and obtaining a grayscale design that relates to the porosity and the anisotropic elastic modulus;

using reaction diffusion equations to de-homogenize the grayscale design to obtain a pattern for the non-spherical apertures; and manufacturing the elastic metamaterial by forming the pattern for the non-spherical apertures in the solid phase material such that the non-spherical apertures extend through the solid phase material.

2. The method according to claim 1, wherein the gradient-based algorithm comprises a topology optimization problem solved according to constitutive laws associated with a linearly elastic medium.

3. The method according to claim 2, wherein the topology optimization problem is solved maximizing or minimizing a spectral displacement variable or set of variables of the elastic medium.

4. The method according to claim 3, wherein the spectral displacement variable is proportional to a structure root mean square velocity at one or both of a predetermined point and predetermined frequency.

5. The method according to claim 2, wherein the gradient-based algorithm comprises at least one of a method of moving asymptotes (MMA) optimizer for the topology optimization problem and a globally convergent method of moving asymptotes (GCMMA) optimizer for the topology optimization problem.

6. The method according to claim 1, comprising using an anisotropic diffusion tensor with two-component reaction diffusion equations.

7. The method according to claim 6, wherein the step of using reaction diffusion equations with the grayscale design to obtain a pattern of non-spherical apertures comprises extracting a unit cell porosity magnitude plus a tensor-expression of the anisotropic elastic modulus.

8. The method according to claim 6, comprising repeatedly solving the reaction diffusion equations for a time period and alternatively using weakly anisotropic and strongly anisotropic diffusion tensors.

9. The method according to claim 1, wherein a frequency response of the acoustic radiator is variable based on a single-material or multi-material selection design of the acoustic radiator.

10. The method according to claim 1, wherein the step of determining a set of boundary conditions for the plurality of non-spherical apertures comprises using at least one look-up table mapping grayscale design information and unit cell designs to a size and orientation of the non-spherical apertures.

11. The method according to claim 10, wherein the x-axis of the mapping corresponds to a width dimension of the non-spherical aperture in the unit cell, the y-axis corresponds to a height dimension of the non-spherical aperture, and the z-axis is an elastic modulus tensor component.

12. The method according to claim 11, wherein the at least one look-up table is based on data obtained from varying the width dimension and the height dimension of the non-spherical aperture in the unit cell over a range of values and calculating the tensor component.

13. A method for manufacturing an elastic metamaterial for an acoustic radiator, the method comprising:

defining an array of unit cells that form the acoustic radiator, the array including an elastic medium comprising a solid phase material selected from the group consisting of polymers, polymer-based materials, metals, and composite materials, and having an x-axis defining a longitudinal direction, a y-axis defining a transverse direction with respect to the x-axis, and a z-axis perpendicular to both the x-axis and the y-axis;

determining a set of boundary conditions for a plurality of non-spherical apertures defined in the elastic medium of the array, with each non-spherical aperture disposed within a boundary defined by a single respective unit cell of the array;

using a gradient-based algorithm to optimize a porous media model domain for the elastic medium, the gradient-based algorithm comprising a topology optimization problem solved according to constitutive laws associated with a linearly elastic medium, and where porosity is related to size dimensions of the non-spherical aperture and an anisotropic elastic modulus is related to an angle of orientation of the non-spherical aperture;

optimizing an objective function, and obtaining a grayscale design that relates to the porosity and the anisotropic elastic modulus;

using reaction diffusion equations to de-homogenize the grayscale design to obtain a pattern for the non-spherical apertures; and manufacturing the elastic metamaterial by forming the pattern for the non-spherical apertures in the solid phase material such that the non-spherical apertures extend through the solid phase material.

14. The method according to claim 13, wherein the topology optimization problem is solved maximizing or minimizing a spectral displacement variable or set of variables of the elastic medium.

15. The method according to claim 14, wherein the spectral displacement variable is proportional to a structure root mean square velocity at one or both of a predetermined point and predetermined frequency.

16. The method according to claim 13, wherein the gradient-based algorithm comprises at least one of a method of moving asymptotes (MMA) optimizer for the topology optimization problem and a globally convergent method of moving asymptotes (GCMMA) optimizer for the topology optimization problem.

17. The method according to claim 13 further comprising using an anisotropic diffusion tensor with two-component reaction diffusion equations.

18. The method according to claim 17, wherein the step of using reaction diffusion equations with the grayscale design to obtain a pattern of non-spherical apertures comprises extracting a unit cell porosity magnitude plus a tensor-expression of the anisotropic elastic modulus.

19. The method according to claim 17 further comprising repeatedly solving the reaction diffusion equations for a time period and alternatively using weakly anisotropic and strongly anisotropic diffusion tensors.

20. The method according to claim 13, wherein a frequency response of the acoustic radiator is variable based on a single-material or multi-material selection design of the acoustic radiator.

* * * * *